(12) United States Patent
Zhang et al.

(10) Patent No.: US 6,925,252 B2
(45) Date of Patent: Aug. 2, 2005

(54) ELECTRIC HEATING FUMIGATOR

(75) Inventors: Jining Zhang, Beijing (CN); Zhe Zhang, Beijing (CN)

(73) Assignee: Beijing Taiming Science & Information Technology Co., Ltd., Beijing (CN)

( * ) Notice: Subject to any disclaimer, the term of this patent is extended or adjusted under 35 U.S.C. 154(b) by 0 days.

(21) Appl. No.: 10/763,916

(22) Filed: Jan. 23, 2004

(65) Prior Publication Data

US 2004/0170406 A1 Sep. 2, 2004

Related U.S. Application Data

(63) Continuation of application No. PCT/CN02/00510, filed on Jul. 22, 2002.

(30) Foreign Application Priority Data

Jul. 23, 2001 (CN) .......................... 01120560 A

(51) Int. Cl.[7] .............................. F17C 7/04; F27D 11/00
(52) U.S. Cl. ....................................... 392/403; 219/415
(58) Field of Search ................................ 392/386, 389, 392/391, 392, 394, 403, 404, 405, 406; 219/415, 410, 430, 431, 432, 433, 438, 439; 43/129

(56) References Cited

U.S. PATENT DOCUMENTS

| | | | |
|---|---|---|---|
| 2,675,293 A | | 4/1954 | Baker |
| 2,685,020 A | | 7/1954 | Laibow |
| 4,024,377 A | * | 5/1977 | Henke .......................... 219/439 |
| 4,215,267 A | * | 7/1980 | Kaebitzsch .................. 219/439 |
| 4,518,850 A | * | 5/1985 | Grasso ......................... 219/505 |
| 4,675,504 A | * | 6/1987 | Suhajda ....................... 392/390 |
| 4,915,998 A | * | 4/1990 | Parenti et al. ................ 428/76 |

FOREIGN PATENT DOCUMENTS

| | | |
|---|---|---|
| CN | 88 2 11435 U | 12/1988 |
| CN | 99248238.0 | 7/2000 |
| GB | 1 601 095 | 10/1981 |
| JP | 2-39840 U | 3/1990 |

\* cited by examiner

*Primary Examiner*—Sang Paik
(74) *Attorney, Agent, or Firm*—Akin Gump Strauss Hauer & Feld, LLP

(57) ABSTRACT

An electric heating fumigator (100) includes a base (9), a case cover (12) and a heater support (3) mounted on the base (9). A heater (1) is inserted into the heater support (3) and heat-insulation layers (2, 5) are attached to the heater support (3), so that one of them is located between the heater (1) and the heater support (3). The bottom of the support (3) is fixed on the base (9) of the fumigator. The electric heating fumigator provides better heat-insulation and electrical insulation effects, such that it can increase to a higher temperature to heat and discharge a large amount of medicament in a short time in a safe and stable way.

7 Claims, 4 Drawing Sheets

ELECTRIC HEATING FUMIGATOR

CROSS-REFERENCE TO RELATED APPLICATIONS

This application is a continuation of International Application No. PCT/CN02/00510, filed Jul. 22, 2002, the disclosure of which is incorporated herein by reference.

BACKGROUND OF THE INVENTION

The present invention relates to an electric heating fumigator, and more particularly, to an electric heating fumigator for fumigating medicament such as insecticide, antiseptic, air freshener and/or deodorizer.

Currently, many types of electric heating fumigators have been disclosed. The widely used electric heating fumigators, whose heating boards keep the temperature of about 160–180° C., generally achieve the aim of dispelling and killing pests by heating and releasing pyrethrum-like ester insecticide less than 150 milligrams (generally tens of milligrams) within 6–8 hours. Another widely used electric heating fumigator for fumigating liquid medicine, for example, the liquid evaporator disclosed in Chinese Patent CN88211435, also evaporates the liquid medicine contained in a bottle into a relatively closed space over a night, with the heating temperature of 90–170° C.

In addition, GB1601095A disclosed an electric heating fumigator, wherein the insecticide and porous inorganic materials are extruded together so as to make the insecticide spread into the porous carrier and as a result, the surface for volatilization is enlarged, and the activated ingredient volatilizes rapidly with the porous medicament containing pyrethrum-like ester insecticide heated up to 200–430° C. by the heating updraft.

CN99248238.0 disclosed an electric heating fumigator comprising a movable inner cup, a mid cup with heating elements, a mid cup base and a housing, the inner cup directly contacts with the heating elements embedded in the mid cup, which enables an excellent fumigating effect by heating the pesticide in the cup to 200–350° C. and evaporating it in a closed space to get a relatively high concentration in a relatively short time.

However, the above-mentioned electric heating fumigators cannot evaporate medicament rapidly in a short time at the the relatively low temperature, which makes them actually unusable in some large spaces such as storehouse, greenhouse, etc. and some medicament such as some kinds of pesticide cannot reach their volatilizing points at the temperature below 200° C. Therefore, these electric heating fumigators fail to achieve the desired effect of preventing insect pests. Moreover, their performances of electric insulation, heat insulation, safety and so on at relatively high temperature are still unsatisfactory. Thus, an electric heating fumigator with excellent fumigating effect and safe electric performance is needed, which with a high heating temperature, can discharge a large amount of medicament in a short time, kill a variety of insects and get a relatively high medicament concentration rapidly.

BRIEF SUMMARY OF THE INVENTION

An object of the present invention is to provide an electric heating fumigator with better heat and electric insulation performance, which overcomes the shortcomings of prior art and allows a higher heating temperature and an ability of discharging a large amount of medicament in a short time in a safe and stable way.

Particularly, the present invention provides an electric heating fumigator with the heating temperature exceeding about 200° C., for example about 200–500° C., which comprises a base and a case cover as well as a heater support mounted on the base; a heater is inserted into the heater support; wherein a heat-insulation layer is attached to the heater support and located between the heater and the heater support and the bottom of the heater support is fixed on the base of the fumigator.

In another preferred embodiment, the inside and outside of the heater support is provided with an inner heat-insulation layer, which is located between the heater and the heater support, and an outer heat-insulation layer, via which the upper portion of the heater support contacts with the case cover of the fumigator.

In a further preferred embodiment, the heater support is hollow and holds a heat spreader such as a fan, and the upper portion of the heater support is provided with holes towards the heater to ensure that the air is blown to the heater smoothly, so as to make the volatilized medicament rise upwards.

In the electric heating fumigator according to the present invention, the heater is designed to directly contact with the heat-insulation layers for the purpose of preventing the overheating of the inside and the housing of the fumigator. The heat-insulation layers are made of polytetrafluoroethylene, silicone rubber, or ceramic. The heater support is made of metal.

The electric heating fumigator according to the present invention may also comprise the components including a case cover, an upper cover, a housing, a filter screen, a transformer, a timer, a circuit board, an indicator light, a knob of the timer, and the like.

With regard to the electric heating fumigator according to the present invention, in a specific design, the heater support fixed on the base divides the fumigator into two chambers, one of which is a heat-insulation chamber equipped with a heat spreader, for example a fan, the inner heat-insulation layer, the heater, the heater support, and the outer heat-insulation layer, and the other one of which is a control chamber equipped with a circuit board, a transformer, a timer controlling the time and power switch, a power supply wire connected to the underside of the fumigator, wherein the heater conductor is connected to the circuit board through a conductor hole of the inner heat-insulation layer, the conductor of the heat spreader, such as a fan, is connected to the transformer, the power supply wire and the timer are directly connected to the circuit board, the circuit board is fixed on the base of the fumigator, and the conductor of the transformer is connected with the circuit board.

The case cover is set on the base. The optional filter screen is located between the base and the case cover. The case cover is connected with an optional housing, preferably a transparent housing. The housing may further be provided with an optional upper cover, preferably, a transparent upper cover, which can be taken away when the fumigator is in operation. A timer for controlling time and power switch is installed on the side of the case cover, wherein an indicator light is provided to indicate working modes.

In the electric heating fumigator according to the present invention, the heat-insulation layer is located between the heater and the heater support. Within the heater support, a heat spreader, for example a fan, is installed on one side. The upper portion of the heater support is provided with holes towards the heater to ensure that the air is blown to the heater smoothly.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

The preferred embodiments will now be described with reference to the accompanying drawings.

Figure 1:
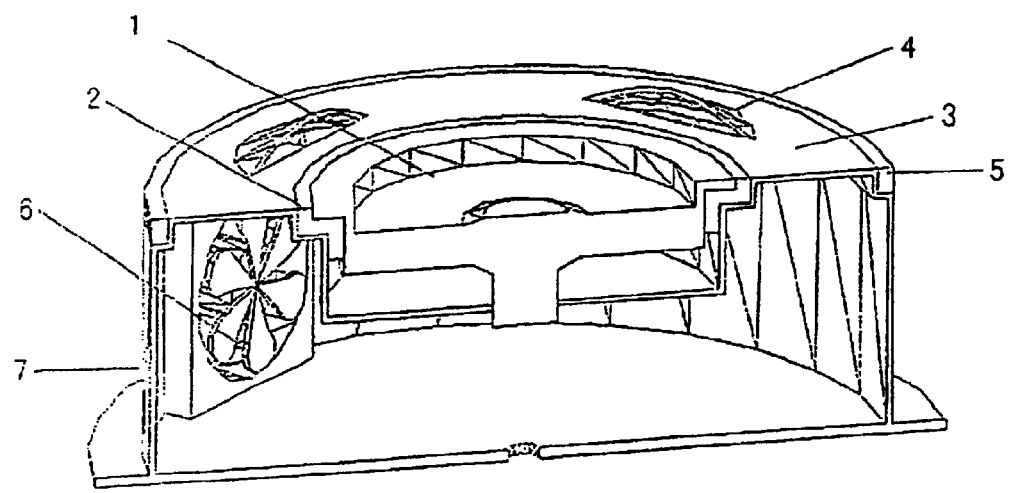
FIG. 1 is a schematic sectional side perspective view of the electric heating fumigator of and embodiment of the present invention showing the inner structure for heat insulation.
Figure 2:
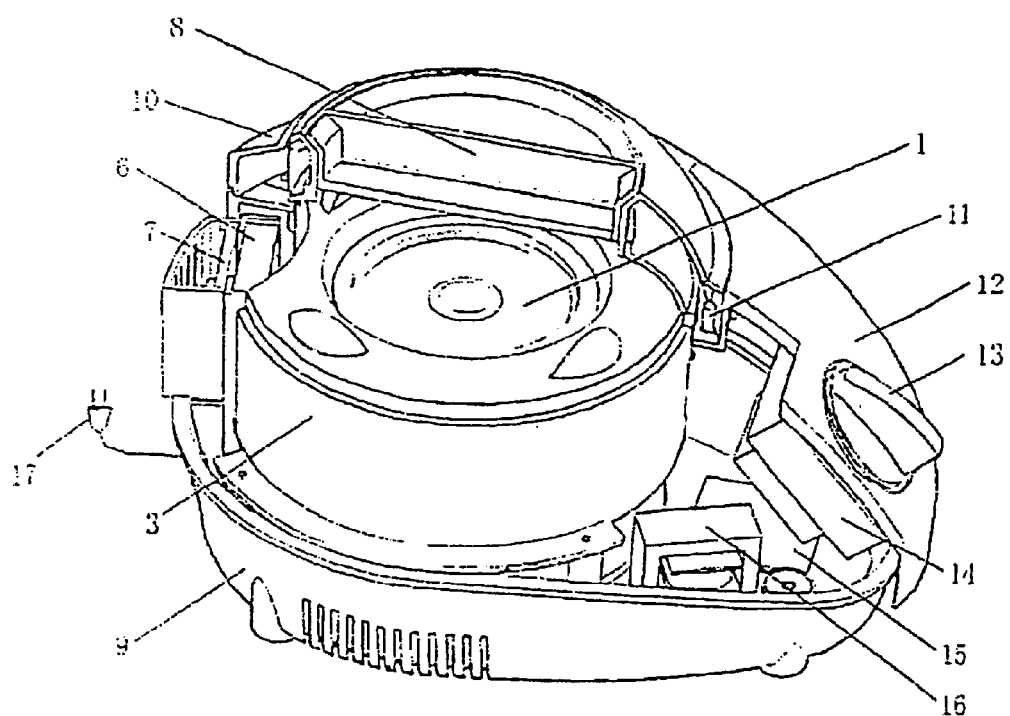
FIG. 2 is another sectional side perspective view of the electric heating fumigator of an embodiment of the present invention.

FIG. 1 is a schematic section view of the heat insulation configuration of the electric heating fumigator 100 according to the present invention, and FIG. 2 is a side section view of the electric heating fumigator 100. It can be seen that the electric heating fumigator 100 comprises a base 9 and a case cover 12, wherein the case cover 12 may be installed onto the base 9 by bolts or other known means (not shown) to form an inner chamber. In this chamber, a heater support 3 is mounted on the base 9 such that the inner chamber of the electric heating fumigator 100 is partitioned into two chambers. One is a heating and insulating chamber, as shown in FIG. 1, in which a fan 6, an inner heat insulation loop 2, a heater 1, a heater support 3 and an outer heat insulation loop 5 are fixedly positioned. The other is a heat insulation chamber, as shown in FIG. 2, installed with a circuit board 15 and a transformer 16. The case cover 12 mounted on the heat insulation chamber is installed with a timer 14 for controlling time and power switch. A power supply wire 17 is connected to the underside of the case cover. An indicator light 11 is provided to indicate the working modes. A filter screen 7 is installed between the base 9 and the case cover 12. The case cover 12 is provided with a transparent housing 10. The housing 10 may be provided with a transparent upper cover 8, which can be taken away in operation.

In the electric heating fumigator 100 according to the present invention, the heat insulation part is composed of the inner heat insulation loop 2 serving as the inner heat-insulation layer, the heater support 3, and the outer heat insulation loop 5 serving as the outer heat-insulation layer. The inner heat-insulation loop 2 is located between the heater 1 and the heater support 3, and the outer heat-insulation loop 5 is fixed to the outside of the heater support. The fan 6 is installed inside the heater support 3. The filter screen 7 is optionally positioned outside the fan 6. The upper portion of the heater support 3 is provided with a plurality of holes 4 towards the heater 1 to ensure that the wind is blown to the heater 1 smoothly. The holes are not limited in terms of number and shape. The heater 1 is fixed to the heater support 3 by the heat-insulation loops. The conductor of the heater is connected to the circuit board 15 through a conductor hole of the heat-insulation structure (not shown), the conductor of the fan 6 is connected to the transformer 16, the power supply wire 17 and the timer 14 are directly connected to the circuit board 15, the circuit board 15 is fixed on the base 9 of the fumigator, and the conductor of the transformer 16 is connected with the circuit board 15. The above-described connection relationships are conventional means and are well known to those skilled in the art, therefore, they will not be described in details herein.

The heat insulation structure may use single layer or multi-layer heat insulators, preferably those composed of more than two layers. The heater support 3 is hollow, in which a heat spreader is preferably installed, such as an axial fan or a micro fan. The heat-insulation materials can be selected from various materials that will not melt at relatively high temperature. The inner heat-insulation loop 2 and the outer loop 5 are preferably made of heat-insulation materials such as polytetrafluoroethylene, silicone rubber, or ceramic etc., more preferably silicone rubber. The heat support 3 may be made of various heat-resistant rubber and ceramic, especially metals such as steel, aluminum alloy and the like.

In this description, the term "heater" refers to the component heated by electrical current. All heaters with power more than 10W are applicable. The power supply may be direct or alternating current. The heaters supplied by alternating current and with power more than 50W are preferred, and the heating cups are manufactured in such a way that the medicament container and the heater are integrated into a whole part are particularly preferred. For example, the heater 1 may be a resistance coil, PTC, or a heating cup commercially available with the medicament container and the heater formed as a unitary part.

In this description, the term "heater support" refers to the part used to support the heater and to combine the heater and the base of the fumigator. Generally, the heater support 3 is separated from the base 9, and under special circumstances, for example, when the heater support 3 is made of the same material with the base 9, it may also be molded with the base 9 as a unitary part. The shape of the heater support 3 is not critical, as long as it can support the heater 1 and separate the heater 1 from the base 9, so as to prevent the overheating of the inside and the cover of the fumigator.

The underside of the base 9 may be provided with a plurality of holes and feet for balanced position. The base 9 may be of various shapes, as long as it is helpful for locating the heater support and other components defined inside.

In the electric heating fumigator 100 according to the present invention, the heater 1 itself may be a container of tablets or liquid medicine to be fumigated, which may be of flat plate or cup, or other different shapes.

Figure 3:
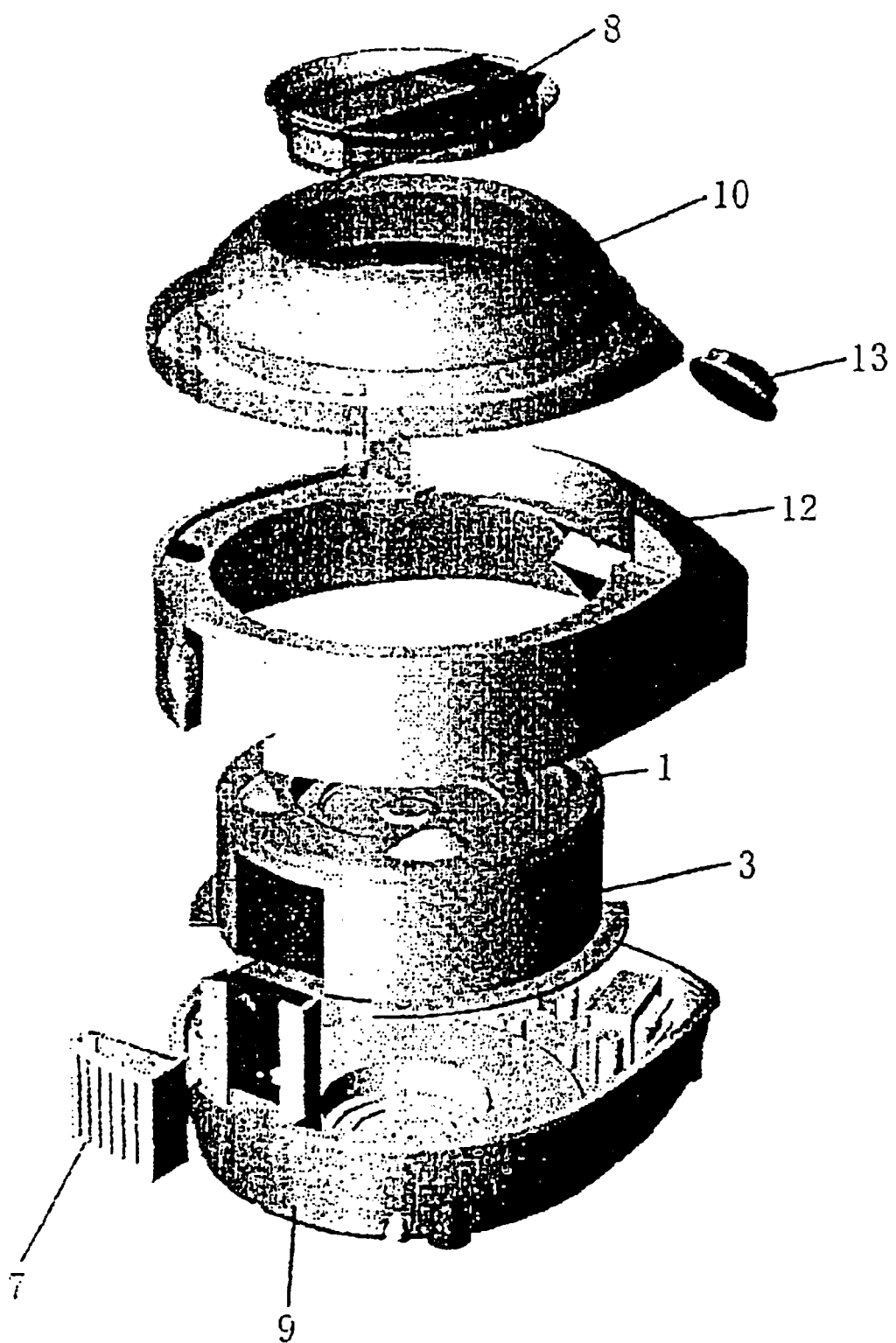
FIG. 3 is a perspective exploded view of the electric heating fumigator.
Figure 4:
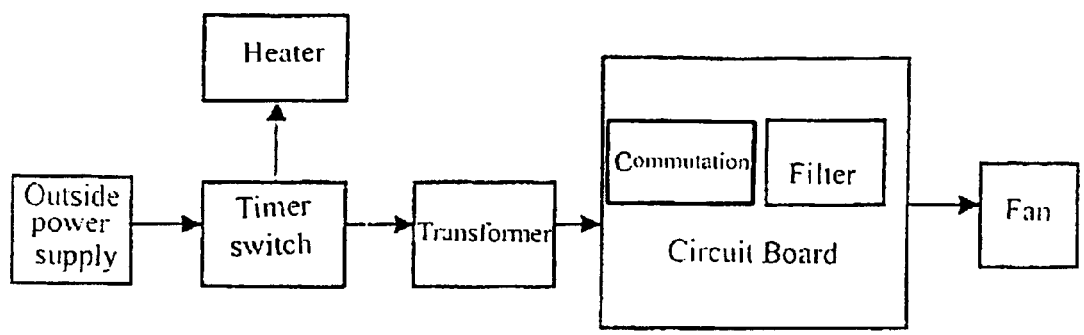
FIG. 4 is a block diagram of the circuit of the electric heating fumigator.

According to the present invention, the heating time and the rotation of the fan is controlled by the control circuit as shown in FIG. 3. The external power supply is divided into two flows by the timer 14, one of which is supplied to the heater, and the other is transformed by the transformer and then is supplied to the fan after commutation and filter.

All electric components used in this invention such as the transformer 16, the timer 14, the circuit board 15, etc, are known to those skilled in the art. They can select and use different commercially available products, depending on the designed electric heating fumigator and based on general technical knowledge or experimental results.

The electric heating fumigator of the present invention is suitable for using in houses, hotels, restaurants and the like for preventing and killing pests and bacteria.

The electric heating fumigator of the present invention can heat medicament to a temperature above about 200° C., for example about 200–500° C., so that fumigant evaporates rapidly and the activated ingredient volatilizes under the high temperature of the heater and spreads into each corner and seal of the closed space in a short time. Therefore, pests can be prevented and killed in a simple and clean way in a short time without pollution. For black beetles, fumigant used generally amounts to about 10–80 mg/m$^3$, preferably about 40–60 mg/m$^3$; for flying insects for example mosquitoes, fumigant used generally amounts to about 3–20 mg/m$^3$, preferably about 5–10 mg/m$^3$; and for flies, fumigant used generally amounts to about 5–30 mg/m$^3$, preferably about 10–15 mg/m$^3$.

Compared with the prior art, the electric heating fumigator of the present invention can evaporate fumigant more rapidly, so that the fumes of activated ingredient spread into each corner and reach the whole space at a high concentration in a short time. The activated ingredient reaches the pests in the form of minute particles and makes the pests faint and die.

The operation process and principle of the electric heating fumigator of the present invention will be described herein. At first, fumigant is put into the heater 1, the amount thereof should be determined depending on the area of the room and the breed of pests, and then the fumigator is switched on. The timer knob 14 is turned to switch the indicator light 11 on. The heater 1 is heated and reaches a temperature above about 200° C. rapidly. Fumigant evaporates at different temperatures, and the fumigant concentration in the closed space increases in a short time so as to kill mosquitoes, flies, and black beetles. The power supply is switched down automatically when it arrives at the predetermined time.

EXAMPLE 1

Test Experiment of Internal and External Temperatures of the Fumigator

After the fumigator has been supplied with power for a half hour, the measurement of the temperature is carried out with an electronic thermometer. Within the internal side of the fumigator, the temperature of the heater, the timer in the case cover, and the circuit board are measured. For the external surface of the fumigator, five points of the case cover are measured.

TABLE 1

| Part or point measured | Heater | Timer | Circuit board | Front of external surface | Left side of external surface | Right side of external surface | Back of external surface | Top of the transparent housing |
|---|---|---|---|---|---|---|---|---|
| Temp (° C.) | >200 | 59 | 58 | 55 | 57 | 57 | 53 | 62 |

EXAMPLE 2

Experiment for Killing German Beetles

The medicament used is 96% TAIMING electric heating tablet for killing black beetles. The amount of medicament is 80 mg/m3. The pests used for experiment are German Beetles.

TABLE 2

| Number of beetles | Dosage of fumigant (mg/m3) | Volume of room (m3) | KT50 (min) | KT95 (min) | Mortality in 24 hours |
|---|---|---|---|---|---|
| 38 | 80 | 15 | 14 | 32 | 100% |

EXAMPLE 3

Field Test for Killing Germany Beetles

The medicament used is 96% TAIMING electric heating tablet for killing black beetles. The amount of medicament is 1.5 g. The pests used for experiment are Germany Beetles.

TABLE 3

| Dosage of fumigant (g) | Volatilizing time (min) | Volatilizing amount (mg/min) | Number of killed beetles |
|---|---|---|---|
| 1.5 | 23 | 66 | 1560 |

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. An electric heating fumigator (100) comprising a base (9), a case cover (12) and a heater support (3) mounted on the base (9), a heater (1) being inserted into the heater support (3), and heat-insulation layers (2, 5) attached to the heater support (3) so that at least one of the layers is located between the heater (1) and the heater support (3), wherein a bottom of the support (3) is fixed on the base (9) of the fumigator, and wherein the heater support (3) is hollow and holds a heat spreader (6), and an upper portion of the heater support (3) is provided with holes (7) towards the heater.

2. The electric heating fumigator (100) according to claim 1, wherein the heater support (3) has an inner heat-insulation layer (2) and an outer heat-insulation layer (5), the inner layer (2) being located between the heater (1) and the heater support (3), and an upper portion of the heater support (3) contacting the case cover (12) via the outer layer (5).

3. The electric heating fumigator (100) according to claim 1, wherein the heat-insulation layers (2, 5) comprise at least one material selected from the group consisting of polytetrafluoroethylene, silicone rubber, and ceramic, and the heater support (3) comprises metal.

4. The electric heating fumigator (100) according to claim 2, wherein the heater support (3) fixed on the base (9) divides the fumigator into two chambers, one chamber being a heat-insulation chamber equipped with a heat spreader, the inner heat-insulation layer (2), the heater (1), the heater support (3), and the outer heat-insulation layer (5), and the other chamber being a control chamber equipped with a circuit board (15), a transformer (16), a timer (14), a power supply wire (17) connected to the underside of the fumigator, in which a conductor of the heater is connected to the circuit board (15) through a conductor hole of the inner heat-insulation layer (2), a conductor of the fan is connected to the transformer (16), a power supply wire (17) and the timer (14) are directly connected to the circuit board (15), the circuit board (15) is fixed on the base (9) of the fumigator, and a conductor of the transformer (16) is connected with the circuit board (15).

5. The electric heating fumigator (100) according to claim 4, wherein an outside of the heat spreader is provided with a filter screen between the base (9) and the case cover (12).

6. The electric heating fumigator (100) according to claim 5, wherein a housing (10) is connected with the case cover (12) and an upper cover (8) is mounted on the housing (10).

7. The electric heating fumigator (100) according to claim 1, wherein the heat-insulation layers (2,5) comprise multi-layer heat insulators.

* * * * *